US007702394B2

(12) United States Patent  
Imran

(10) Patent No.: US 7,702,394 B2  
(45) Date of Patent: Apr. 20, 2010

(54) RESPONSIVE GASTRIC STIMULATOR

(75) Inventor: Mir A. Imran, Los Altos Hills, CA (US)

(73) Assignee: IntraPace, Inc., Mountain View, CA (US)

( * ) Notice: Subject to any disclaimer, the term of this patent is extended or adjusted under 35 U.S.C. 154(b) by 600 days.

(21) Appl. No.: 10/950,345

(22) Filed: Sep. 23, 2004

(65) Prior Publication Data

US 2005/0065571 A1    Mar. 24, 2005

Related U.S. Application Data

(60) Continuation-in-part of application No. 10/290,788, filed on Nov. 7, 2002, now Pat. No. 7,016,735, which is a division of application No. 09/847,884, filed on May 1, 2001, now Pat. No. 6,535,764.

(51) Int. Cl.  
*A61N 1/36* (2006.01)

(52) U.S. Cl. ........................................................ 607/40

(58) Field of Classification Search .................. 607/40, 607/133  
See application file for complete search history.

(56) References Cited

U.S. PATENT DOCUMENTS

| | | | |
|---|---|---|---|
| 3,411,507 A | 11/1968 | Wingrove | 128/422 |
| 3,646,940 A | 3/1972 | Timm et al. | 128/421 |
| 3,662,758 A | 5/1972 | Glover | 128/419 |
| 3,677,251 A | 7/1972 | Bowers | 128/419 |
| 3,735,766 A | 5/1973 | Bowers et al. | 128/419 |
| 3,796,221 A | 3/1974 | Hagfors | 128/421 |
| 3,815,611 A | 6/1974 | Denniston, III | 128/419 |
| 3,835,865 A | 9/1974 | Bowers | 128/419 |
| 4,102,344 A | 7/1978 | Conway | 128/419 |
| RE30,366 E | 8/1980 | Rasor et al. | 128/419 |
| 4,628,928 A | 12/1986 | Lowell | 128/303 |
| 4,823,808 A | 4/1989 | Clegg | 128/773 |
| 4,921,481 A | 5/1990 | Danis et al. | 604/67 |
| 4,925,446 A | 5/1990 | Garay | 604/96 |
| 5,188,104 A | 2/1993 | Wernicke et al. | 128/419 |

(Continued)

FOREIGN PATENT DOCUMENTS

EP        0129483        12/1984

(Continued)

OTHER PUBLICATIONS

C. Paul Swain, et al., An Endoscopically Deliverable Tissue-Transfixing Device for Securing Biosensors In The Gastrointestinal Tract, *Gastrointestinal Endoscopy*, 40/6:730-734 (1994).

(Continued)

*Primary Examiner*—George R Evanisko  
*Assistant Examiner*—Alyssa M Alter  
(74) *Attorney, Agent, or Firm*—Townsend and Townsend and Crew LLP

(57) ABSTRACT

A responsive gastrointestinal stimulation device is provided where one or more sensors sense data corresponding to a subject or the gastrointestinal tract of a subject and responds to sensing the data by stimulating, adjusting stimulation, or stopping stimulation of the gastrointestinal tract. A stimulation device is also provided to stimulate the gastrointestinal tract to produce a sensation of satiety or to control hunger or food consumption.

9 Claims, 8 Drawing Sheets

U.S. PATENT DOCUMENTS

| | | | |
|---|---|---|---|
| 5,197,491 A | 3/1993 | Anderson et al. | 128/786 |
| 5,217,449 A | 6/1993 | Yuda et al. | 604/890 |
| 5,292,344 A * | 3/1994 | Douglas | 607/40 |
| 5,415,181 A | 5/1995 | Hogrefe et al. | 128/736 |
| 5,423,872 A | 6/1995 | Cigaina | 607/40 |
| 5,540,730 A | 7/1996 | Terry et al. | 607/40 |
| 5,558,640 A | 9/1996 | Pfeiler et al. | 604/67 |
| 5,690,691 A * | 11/1997 | Chen et al. | 607/40 |
| 5,716,392 A | 2/1998 | Bourgeois et al. | 607/132 |
| 5,792,048 A | 8/1998 | Schaefer | 600/302 |
| 5,800,445 A | 9/1998 | Ratcliff et al. | 606/116 |
| 5,836,994 A | 11/1998 | Bourgeois | 607/40 |
| 5,861,014 A | 1/1999 | Familoni | 607/40 |
| 5,928,195 A | 7/1999 | Malamud et al. | 604/141 |
| 5,993,473 A | 11/1999 | Chan et al. | 606/192 |
| 5,995,872 A | 11/1999 | Bourgeois | 607/40 |
| 6,026,326 A | 2/2000 | Bardy | 607/40 |
| 6,041,258 A | 3/2000 | Cigaina et al. | 607/40 |
| 6,083,249 A | 7/2000 | Familoni | 607/40 |
| 6,091,992 A | 7/2000 | Bourgeois | 607/40 |
| 6,097,984 A | 8/2000 | Douglas | 607/40 |
| 6,098,629 A | 8/2000 | Johnson et al. | 128/897 |
| 6,104,955 A | 8/2000 | Bourgeois | 607/40 |
| 6,115,635 A | 9/2000 | Bourgeois | 607/40 |
| 6,205,359 B1 | 3/2001 | Boveja | 607/45 |
| 6,216,039 B1 | 4/2001 | Bourgeois | 607/40 |
| 6,243,607 B1 | 6/2001 | Mintchev et al. | 607/40 |
| 6,285,897 B1 | 9/2001 | Kilcoyne et al. | |
| 6,321,124 B1 | 11/2001 | Cigaina | 607/133 |
| 6,327,503 B1 | 12/2001 | Familoni | 607/40 |
| 6,366,814 B1 | 4/2002 | Boveja et al. | 607/45 |
| 6,381,495 B1 | 4/2002 | Jenkins | 607/40 |
| 6,427,089 B1 | 7/2002 | Knowlton | |
| 6,449,511 B1 | 9/2002 | Mintchev et al. | 607/40 |
| 6,453,199 B1 | 9/2002 | Kobozev | 607/40 |
| 6,454,785 B2 | 9/2002 | DeHoyos Garza | |
| 6,477,423 B1 | 11/2002 | Jenkins | 607/40 |
| 6,510,332 B1 | 1/2003 | Greenstein | 600/377 |
| 6,529,778 B2 | 3/2003 | Prutchi | 607/119 |
| 6,540,789 B1 | 4/2003 | Silverman et al. | 623/23.65 |
| 6,542,776 B1 | 4/2003 | Gordon et al. | 607/40 |
| 6,564,101 B1 | 5/2003 | Zikria | 607/40 |
| 6,571,127 B1 | 5/2003 | Ben-Haim et al. | 607/40 |
| 6,591,137 B1 * | 7/2003 | Fischell et al. | 607/40 |
| 6,600,953 B2 | 7/2003 | Flesler et al. | 607/40 |
| 6,606,518 B1 | 8/2003 | Cigaina | 607/41 |
| 6,606,523 B1 | 8/2003 | Jenkins | 607/133 |
| 6,609,025 B2 | 8/2003 | Barrett et al. | 607/2 |
| 6,611,715 B1 | 8/2003 | Boveja | 607/40 |
| 6,615,084 B1 | 9/2003 | Cigaina | 607/40 |
| 6,684,104 B2 | 1/2004 | Gordon et al. | 607/40 |
| 6,826,428 B1 | 11/2004 | Chen et al. | 607/40 |
| 6,879,859 B1 | 4/2005 | Boveja | 607/45 |
| 6,895,278 B1 | 5/2005 | Gordon | 607/40 |
| 6,895,279 B2 | 5/2005 | Loeb et al. | 607/40 |
| 7,020,526 B1 | 3/2006 | Zhao | |
| 7,054,692 B1 | 5/2006 | Whitehurst et al. | |
| 2002/0072780 A1 | 6/2002 | Foley | 607/40 |
| 2002/0103424 A1 | 8/2002 | Swoyer et al. | 600/350 |
| 2002/0103521 A1 | 8/2002 | Swoyer et al. | 607/116 |
| 2002/0103522 A1 | 8/2002 | Swoyer et al. | 607/116 |
| 2002/0161414 A1 * | 10/2002 | Flesler et al. | 607/40 |
| 2002/0198570 A1 | 12/2002 | Puskas | 607/40 |
| 2002/0198571 A1 | 12/2002 | Puskas | 604/2 |
| 2003/0055463 A1 | 3/2003 | Gordon et al. | 607/40 |
| 2003/0120328 A1 | 6/2003 | Jenkins | 607/2 |
| 2003/0144708 A1 | 7/2003 | Starkebaum | 607/116 |
| 2003/0195600 A1 | 10/2003 | Tronnes | 607/133 |
| 2003/0212439 A1 | 11/2003 | Schuler et al. | 607/40 |
| 2004/0015201 A1 | 1/2004 | Greenstein | 607/40 |
| 2004/0059393 A1 | 3/2004 | Policker et al. | 607/40 |
| 2004/0088022 A1 | 5/2004 | Chen | 607/40 |
| 2004/0093039 A1 | 5/2004 | Schumert | 607/40 |
| 2004/0133089 A1 | 7/2004 | Kilcoyne et al. | 600/350 |
| 2004/0147816 A1 * | 7/2004 | Policker et al. | 600/300 |
| 2004/0162945 A1 | 8/2004 | King et al. | 607/40 |
| 2004/0167583 A1 | 8/2004 | Knudson | 607/40 |
| 2004/0172084 A1 | 9/2004 | Knudson | 607/40 |
| 2004/0172085 A1 | 9/2004 | Knudson | 607/40 |
| 2004/0172086 A1 | 9/2004 | Knudson | 607/40 |
| 2004/0172088 A1 | 9/2004 | Knudson | 607/40 |
| 2004/0172095 A1 | 9/2004 | Jenkins | 607/116 |
| 2004/0176812 A1 | 9/2004 | Knudson | 607/40 |
| 2004/0236381 A1 | 11/2004 | Dinsmoor | 607/40 |
| 2004/0236382 A1 | 11/2004 | Dinsmoor | 607/40 |
| 2005/0021101 A1 | 1/2005 | Chen et al. | 607/40 |
| 2005/0038454 A1 | 2/2005 | Loshakove | 606/153 |
| 2005/0049655 A1 | 3/2005 | Boveja | 607/58 |
| 2005/0055039 A1 | 3/2005 | Burnett et al. | |
| 2005/0096514 A1 | 5/2005 | Starkebaum | |
| 2005/0113880 A1 | 5/2005 | Gordon et al. | 436/106 |
| 2005/0131486 A1 | 6/2005 | Boveja | |
| 2005/0131487 A1 | 6/2005 | Boveja | |
| 2005/0137643 A1 | 6/2005 | Mintchev | |
| 2005/0149141 A1 | 7/2005 | Starkebaum | 607/40 |
| 2005/0149142 A1 | 7/2005 | Starkebaum | 607/40 |
| 2005/0149146 A1 | 7/2005 | Boveja | |
| 2005/0159800 A1 | 7/2005 | Marshall | 607/122 |
| 2005/0159801 A1 | 7/2005 | Marshall | 607/122 |
| 2005/0222637 A1 | 10/2005 | Chen | |
| 2005/0222638 A1 | 10/2005 | Foley | 607/40 |
| 2005/0251219 A1 | 11/2005 | Evans | |
| 2006/0020298 A1 | 1/2006 | Camilleri et al. | |
| 2006/0025654 A1 | 2/2006 | Suzuki | |
| 2006/0036293 A1 | 2/2006 | Whitehurst et al. | |
| 2006/0058851 A1 | 3/2006 | Cigaina | |
| 2006/0074335 A1 | 4/2006 | Ben-Oren | |
| 2006/0085054 A1 | 4/2006 | Zikorus et al. | |
| 2006/0089571 A1 | 4/2006 | Gertner | |
| 2006/0116736 A1 | 6/2006 | DiLorenzo | |

FOREIGN PATENT DOCUMENTS

| | | |
|---|---|---|
| EP | 0571938 | 6/1988 |
| WO | WO9843700 | 10/1998 |
| WO | 9853878 | 12/1998 |
| WO | WO0030534 | 6/2000 |
| WO | 0158389 | 8/2001 |
| WO | 0176690 | 10/2001 |
| WO | WO 0176690 | 10/2001 |
| WO | WO0226101 | 4/2002 |

OTHER PUBLICATIONS

Keith E. Kelly, et al., Pacing The Canine Stomach With Electric Stimulation, *Am. J. of Physiology*, 222/3:588-594 (Mar. 1972).

J. Chris Eagon et al., Gastrointestinal Pacing, *Surgical Clinics of North America*, 73/6:1161-1172 (Dec. 1993).

Valerio Cigaina, et al., Gastric Myo-Electrical Pacing As Therapy For Morbid Obesity: Preliminary Results.

H. Geldof, et al., Electrogastrographic Study of Gastric Myoelectrical Activity In Patients With Unexplained Nausea And Vomiting, *Gut*, 27:799-808, (1986).

Brent W. Miedema, et al., Pacing The Human Stomach, *Surgery*, 143-150, (Feb. 1992).

Keith A. Kelly, Differential Responses Of The Canine Gastric Corpus And Antrum To Electric Stimulation, *Am. J. of Physiology*, 226/1:230-234, (Jan. 1974).

Electric Stimulation of the Gastrointestinal Tract, GP, p. 151 (Apr. 1964).

Michael P. Hocking, Postoperative Gastroparesis And Tachygastria-Response to Electric Stimulation and Erythromycin, *Surgery*, 114/3:538-542 (Sep. 1993).

Keith A. Kelly et al., Role of the Gastric Pacesetter Potential Defined by Electrical Pacing, *Canadian J. of Physiology and Pharmacology*, 50:1017-1019, (1972).

Babajide O. Familoni, Efficacy of Electrical Stimulation at Frequencies Higher Than Basal Rate in Canine Stomach, *Digestive Diseases and Sciences*, 42/5:892-897, (May 1997).

Bader-Eddine Bellahsene, et al., Evaluation of a Portable Gastric Stimulator, Ninth Annual Conference of the Engineering in Medicine and Biology Society, (1987).

J. Chris Eagon, et al., Effects of Gastric Pacing on Canine Gastric Motility and Emptying, *The American Physiological Society*, 265/4:G767-G774, (Oct. 1993).

Babajide O. Familoni, et al., Electrical Pacing of the Stomach in Dogs.

S. K. Sarna, et al., Electrical Stimulation of Gastric Electrical Control Activity, *Am. J. of Physiology*, 225/1:125-131, (Jul. 1973).

S. K. Sarna, et al., Gastric Pacemakers, *Gastroenterology*, 70:226-231, (1976).

Edwin E. Daniel, et al., Electrical Activity of the Gastrointestinal Tract as an Indication of Mechanical Activity, *Am. J. of Digestive Diseases*, 8/1:54-102, (1963).

M. Kubota, ert al., Manometric Evaluation Of Children With Chronic Constipation Using a Suction-Stimulating Electrode, *Eu. J. Pediari. Surg.*, 2:287-290, (1992).

* cited by examiner

RESPONSIVE GASTRIC STIMULATOR

This application is a Continuation-in-Part application of U.S. Ser. No. 10/290,788 which is a Divisional of U.S. Ser. No. 09/847,884.

FIELD OF THE INVENTION

This invention relates to an implantable device, system and method for controlling electrical stimulation to the stomach wall in response to sensing information.

BACKGROUND OF THE INVENTION

Various organs of the gastrointestinal tract such as the stomach, small intestine and colon contain cells that are believed to govern the organs' periodic contractile behavior. In healthy humans, in certain regions of the organs, these cells generate and propagate rhythmic electrical signals. In general, several types of electrical potential activity have been observed in the gastrointestinal tract. Consistent cyclic slow wave or pacesetter potentials have been observed and higher frequency spike activity has been observed that may correspond to some extent with smooth muscle contractile activity and peristalsis. The stomach and digestive system is also controlled by the nervous system that includes a highly complex enteric nervous system and to some extent, the central nervous system. It is believed that when the pacesetter potentials are combined with a chemical or neural excitation of the cells that smooth muscle contractile activity occurs. It is also believed that stimulation of the stomach may effect a subject's sensation of satiety through a complex system involving smooth muscle stimulation or contractions, and neural and chemical pathways.

Obesity has become one of the leading causes of death in the United States. Electrical stimulation has been proposed to treat obesity by causing a feeling of satiety, for example, by altering gastric motility. Some electrical stimulation is believed to interfere with the electrical potential activity of the stomach and to slow the movement of food through the stomach. Electrical stimulation may cause the stomach to retain food for a greater duration. This gastric retention among other factors may induce a sensation of satiety.

Electrical stimulation of the gastrointestinal tract has also been proposed to treat motility related disorders and other gastrointestinal diseases. The electrical stimulation has been proposed in a number of forms or for a number of applications, such as, e.g., pacing, electrical contractile stimulation or other stimulation.

In some disease states, dysrhythmias of the gastric pacesetter potentials may be present. Electrical pacing of gastric pacesetter potentials has been proposed to induce regular rhythms for the pacesetter potentials with the intent of inducing regular or controlled gastric contractions. The result of abnormal pacesetter potentials may be gastric retention of food. Electrical stimulation of gastric tissue has also been proposed to induce peristalsis. Electrical stimulation has also been proposed to slow the gastric emptying to treat a disorder known as dumping syndrome where the stomach empties at an abnormally high rate into the small intestine causing various gastrointestinal disorders.

An early attempt at a gastric stimulation device included an electrode at the end of a nasogastric tube or catheter. The nasogastric tube was passed into the stomach transnasally. Electrical stimulation was applied using an external stimulator unit through the electrode on the end of the tube. The return electrode was placed on the abdomen. This device required a transnasal procedure whenever stimulation was required.

Other devices used to pace the stomach have generally been implanted by accessing the outside of the stomach through an opening in the abdomen, either through open surgery or laparoscopic surgery. Electrodes have been attached to the stomach laparoscopically with attached leads extending through the abdomen to a subcutaneously or submuscularly implanted electronics unit. The devices may be anchored into the subcutaneous or sub-muscular pocket initially by a suture anchor and/or eventually by fibrous tissue ingrowth around the unit.

Other devices are described, for example in related U.S. Pat. No. 6,535,764, fully incorporated herein by reference. U.S. Pat. No. 6,535,764 describes a gastric stimulator that is implanted by delivering the device through the esophagus of a subject and attaching to the stomach wall from the inside of the stomach. Also, related U.S. patent application Ser. No. 10/109,296, fully incorporated herein by reference, describes a gastric stimulator that is implanted submucosally within the stomach wall.

Some gastric stimulation procedures have proposed electrical stimulation in response to sensing innate electrical pulses within the stomach that fall within particular ranges. According to these procedures, sensing electrical signals are indicators of when or how to stimulate or when or how to stop stimulation. Additionally, a device has been proposed to sense electrical parameters to determine the fullness of an organ and the absence of muscular contraction, and to deliver electrical muscular contraction stimulation to the organ in response (i.e., presumably to treat gastro-paresis). However, some sensed electrical signals are not reliably detected and have not always corresponded with appropriate indicators of need for stimulation.

A gastrointestinal stimulator has be described that senses food being swallowed by sensing motion (with an accelerometer), temperature, or pressure and responsively stimulates to coordinate contractions in various gastrointestinal organs to prevent esophageal acid reflux or, to increase speed of movement of food through the gastrointestinal tract (under the theory that less food will be absorbed when food moves more quickly through the stomach). As described, the stimulator stimulates when the gastrointestinal tract fails to act normally. While there has been some success in gastric stimulation, it is believed that over time the stomach may become desensitized to ongoing stimulation. Therefore, it would be desirable to provide a gastric stimulator that reduces desensitization of the stomach from ongoing stimulation.

Also, implanted stimulators have limited battery life, particularly when the device is smaller. Accordingly, it would be desirable to provide a device that operates to conserve battery life.

It would be desirable to provide a gastric stimulator that stimulates the stomach under predetermined circumstances or conditions or at appropriate times.

It would further be desirable to provide such a stimulator that stimulates in order to produce a sensation of satiety.

Furthermore, to control eating disorders or to treat obesity, it would be desirable to provide a stimulator that senses when food has been ingested and/or can regulate stomach contractions based on identification of the contents of the stomach or according to an eating regimen.

SUMMARY OF THE INVENTION

The present invention provides a device, system and method for treating and/or diagnosing gastric disorders by applying an electrical signal or an electromagnetic field to tissue of the stomach for a therapeutic and/or diagnostic purpose. The invention also provides a device, system and method for treating and/or diagnosing gastric disorders upon sensing one or more parameters, whereupon the device, system or method stimulates the stomach, i.e., on-demand. The diagnostic or therapeutic purpose may include, but is not limited to, controlling appetite, satiety, eating habits and/or obesity, treating nausea, facilitating or expediting mixing or breaking down of food matter or liquids in the stomach, controlling, facilitating or expediting movement of food matter or liquids through the stomach and into the small intestine; and stimulating the stomach to delay passage of food from the stomach and into the small intestine. The stimulation may affect the smooth muscle contractions, nerves associated with the stomach and/or biochemistry or secretions at the stomach.

The invention also provides a device and method for optimizing or adjusting stimulation parameters in response to feedback from sensors.

In accordance with the invention, the device is controlled under predetermined circumstances, conditions, or at predetermined times, by modifying or turning on/off stimulation. Accordingly, the device comprises one or more sensors for sensing a particular parameter, and one or more responsive elements that determines a particular condition or circumstance based on sensing at least one parameter, and that responds to sensing and/or determining a condition or circumstance. One such response may be to cause the device to modify or turn on/off stimulation.

The sensors and responsive elements may include but are not limited to a number of types of sensors and responsive elements and any combination thereof. Sensing may be used over time to identify patterns diagnose diseases and evaluate effectiveness of various treatment protocols. According to the invention, sensors may be included in the device or separately. The stimulation device may be programmed to deliver stimulation in response to sensed parameters. The sensors may sense a plurality of parameters in order to determine whether or not to stimulate or otherwise respond.

For example, a temperature sensor may sense a change in temperature or a rate of change in temperature that indicates ingestion of food or liquid. A pH sensor may be used to determine when food has been ingested or to determine when a subject is hungry and has increased acid secretion. When the temperature or pH changes in a manner indicating food ingestion, the stimulation device may be instructed to deliver stimulation pulses to control gastric motility, i.e., to retain food. An optical emitter and sensor may be used to determine the presence and/or composition of such food. Pressure sensors may be used to sense motility patterns, e.g. presence, strength or frequency of contractions. Mean pressure shifts may be observed to identify gastric contractility. A mechanical sensor may sense, for example, stomach wall contractions.

Contractile sensor may include, for example, a piezo-electric, piezo-resistive, or strain gauge sensor positioned to mechanically sense contractions. Alternatively, a polymeric variable resistive device may be used to sense contractions. A screen-printed resistor may be suitable to sense local contraction, e.g., a change in resistive value may occur when the resistor bends contracts or stretches. A variable capacitor constructed of flexible plates may also be used to sense contractions by detecting when and the degree to which the distance between the plates changes due to contractions.

According to one variation, stomach wall contractions are locally sensed with a contraction sensor. The sensor senses contractions in proximity to a local stimulation site, e.g. adjacent or in proximity to a stimulating electrode.

As the stomach contracts, the stomach wall typically becomes thicker. In one embodiment a device is implanted in the stomach wall includes a strain gauge able to sense change in stomach wall thickness. As the stomach contracts, the impedance of the stomach wall changes. In one embodiment, the sensor includes electrodes configured to sense impedance of the stomach wall.

Biochemical sensors may be used to determine presence or quantity/concentration of a particular biochemical substance, for example, stomach acid, enzyme or hormone secretions. The responsive element may responsively stimulate the stomach to control presence or quantities of such secretions. For example, acid secretions may be correlated with hunger. The stomach may be stimulated to reduce hunger and to reduce acid secretions, which may include, e.g., acid, enzymes, or gastric satiety hormones such as Ghrelin.

The stimulation device may also use sensed parameters to program or reprogram the device stimulation program or protocol. For example, measuring impedance changes through a circuit coupled to the electrodes (e.g., delivering a constant current or voltage across the electrodes to determine impedance) or determining the contractile behavior of the stomach using a contraction sensor, in response to stimulation pulses, the effectiveness of the stimulation pulses may be monitored and adjusted or ramped up to provide optimal response. The stimulation program may also include an automatic adjustment in response to changes in pressure measurement.

The responsive devices may comprise one or more sensors and one or more responsive elements that respond to information sensed by the sensors. The responsive element may process the sensor signal and may make a determination of existence of a condition or circumstance and correspondingly respond.

Where a plurality of stimulation electrodes or stimulation sites is present, a plurality of sensors, each adjacent a particular site may be used to sense effectiveness of stimulation at the site. Stimulation parameters at each site or selection of stimulators may be made in response to sensed data.

Stomach contractions are sometimes associated with hunger. The responsive element may respond to contraction sensors that sense stomach contractions, by stimulating to interfere with the stomach contractions or to otherwise cause a sensation of satiety. The stimulation may be directed to slow, stop or reverse the innate peristaltic contractions that tend to move food through the stomach. The responsive element may respond to information sensed by a contraction sensor by adjusting the stimulation. The responsive element may respond to the contraction sensor that senses local contractions adjacent a stimulation electrode by adjusting the stimulation to elicit a different contraction response. Pulse amplitude, pulse width, frequency, burst repetition rate or other parameters may be adjusted.

A responsive element may stimulate the stomach in response to a temperature sensor sensing the temperature within the stomach. The responsive element may determine when the temperature changes to a predetermined degree, at a predetermined rate, for a predetermined time, or a combination of the foregoing, such that it can be determined that food, or other material has been ingested. The stimulation may be directed to cause gastric retention of food for a greater duration, e.g., by interfering with peristaltic contractions and/or the innate electrical potentials of the stomach.

A responsive element may determine from a pH sensors sensing the pH within a stomach, when the pH has changed to a degree, at a rate, and/or over a period of time such that it indicates food or other material has been ingested. Upon such a determination, the responsive element may stimulate to cause gastric retention of food. The pH sensor may also indicate hunger from an increase in gastric secretions. The responsive element may respond by stimulating to produce satiety, to prevent or reduce hunger, or to reduce secretions of the stomach.

A responsive element may respond to the detection of the presence, absence or detected quantity/concentration of a particular biochemical composition, for example, by stimulating the stomach in response to acid or other secretions, to create a sensation of satiety, or to control the secretions.

A responsive element may determine from sensed impedance of materials in the stomach, when certain types of food have been ingested. Based on the impedance characteristics of the contents of the stomach, the responsive element may determine when and how to stimulate.

A motion sensor or accelerometer may be used to sense movement relating to respiration or gross subject movement, and, based on such information, a responsive element may determine when a subject is sleeping and turn off stimulation. Alternatively, the responsive device may determine when a subject's activity level is at an optimal level for stimulation, and only stimulate at such time. For example, the responsive element may determine when an activity level is either sleeping or relatively higher level of exertion, based on decreased or increased respiration and/or gross movement characteristic of such activity levels. The responsive element may turn off or prevent turning on stimulation in response to sensing certain parameters and determining the existence of such conditions.

The responsive element may determine from a contraction sensor that the stomach is contracting to a given degree or at a given rate and in response, stimulate the stomach to interfere with contractions, or, where contractions may correlate to hunger, stimulate to cause a sensation of satiety.

An optical sensor along with a light source may be located within the stomach. The light source is configured to emit light, and an optical sensor is configured to either sense reflected light or to sense light transmitted through material located in the stomach. The sensor may be configured to sense light at predetermined wavelengths or the light source may emit light at predetermined wavelengths. The contents of the stomach may be qualitatively assessed based on the amount of light at one or more wavelengths that is transmitted or reflected. The composition of the food may be determined based on the light reflecting or transmission characteristics of such food. Various characteristics of food or other material may be determined by emitting light at various food samples and determining characteristic light transmission or reflectance properties. This properties have been determined using food spectroscopy techniques.

The stimulating (or diagnostic) device of the present invention typically includes stimulating electrodes attached or electrically coupled to the stomach. The device may include, for example, electrical circuitry residing within the patient's stomach or leads attached to the stomach and extending through the patient's body to a subcutaneous electronics unit.

In one variation, the device includes: at least one stimulating electrode in electrical contact with the stomach wall; an electronics unit containing the electronic circuitry of the device; and an attachment mechanism for attaching the device to the stomach wall. One or more stimulating electrodes may be secured to the wall of the stomach by an attachment device. One or more stimulating electrodes may also be located on the electronics unit. The device may include electrodes or a housing with electrodes implanted within the stomach wall, e.g., subcutaneously. Another variation of a stimulator device may include a stimulation device secured to the stomach with flexible leads attached to the preferred stimulation site. Examples of such devices are described in U.S. Pat. No. 6,535,764, and U.S. patent application Ser. Nos. 10/109,296 and 10/116,481 incorporated herein by reference.

The stimulation is provided through at least one pair of bipolar type electrodes. Alternatively, a relatively remote return electrode may be provided in a monopolar type device.

Sensors for sensing various parameters of the stomach or corresponding to a particular condition or circumstance can be included with the electrode assembly or separately. The sensors may be, for example: mounted on an electronics unit attached to a stomach wall, on an attachment mechanism that attaches an electronics unit or an electrode to the stomach wall, on an attachment mechanism that separately attaches or otherwise positions the sensor at the stomach, or by other means, for example, in an independently attached device attached or coupled to the patient within the abdomen or at another location.

The contraction sensors may be used locally with respect to the stimulating electrodes. The contraction sensors may be used to determine ideal or preferred stimulation parameters. The contraction sensors may be used when a device is first implanted to program the stimulator to determine the best response or a preferred response. This may be done by slowly ramping up stimulation until a desired response is elicited. The parameters may be adjusted after the device has been used, to readjust the parameters. The stimulation may be automatically, periodically or continuously readjusted in response to the contraction sensing. Accordingly, a substantially instantaneous response is detectable, i.e. an immediate local response to stimulation may be detected in proximity to the stimulation site.

Sensing may also be used over time to identify patterns, diagnose diseases and evaluate effectiveness of various treatment protocols.

DETAILED DESCRIPTION OF THE DRAWINGS

DETAILED DESCRIPTION OF THE PREFERRED EMBODIMENTS

Figures 1A, 1B:
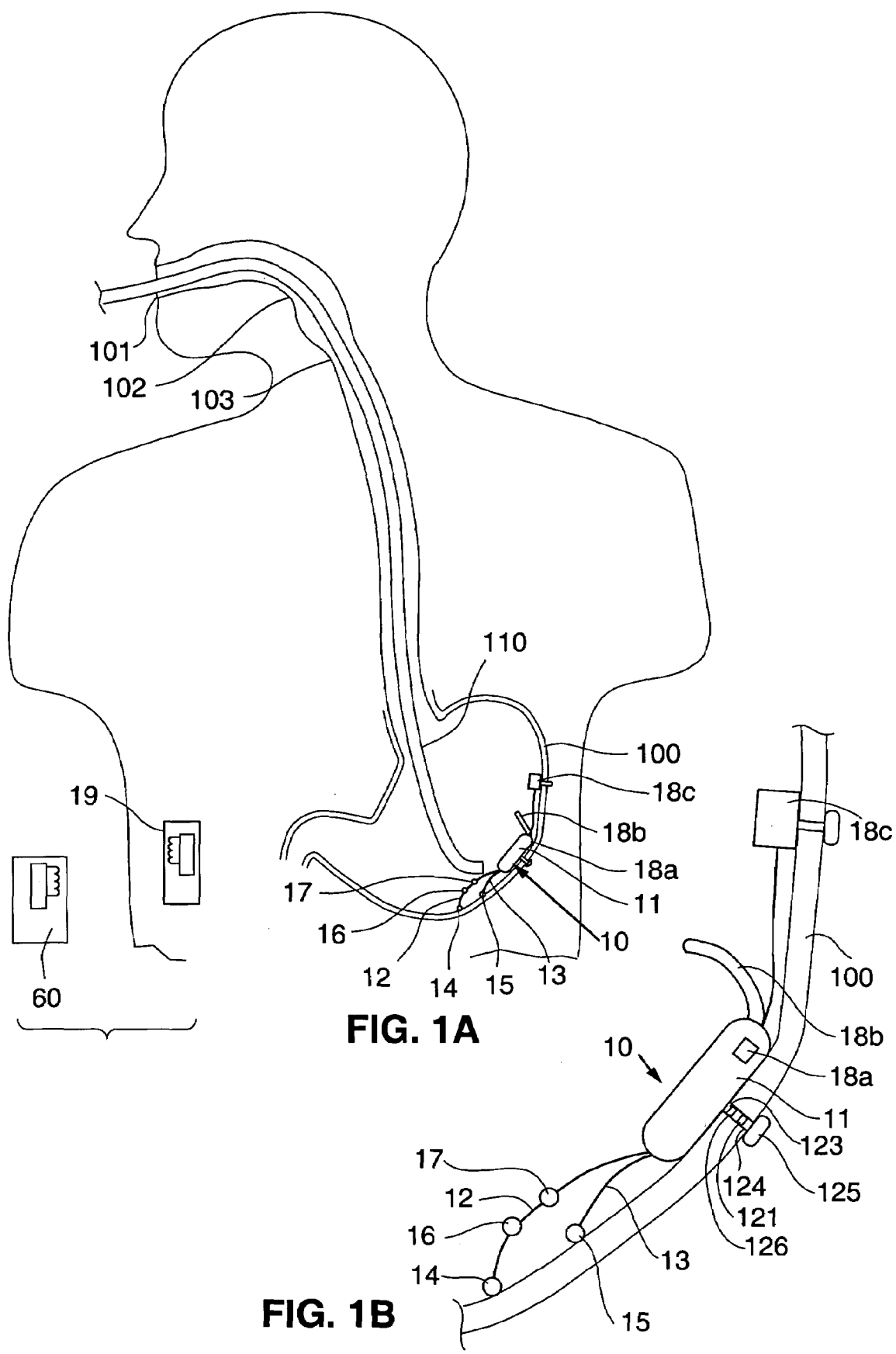
FIG. 1A is a schematic view of a system of an embodiment of the present invention including an electric stimulator as it is implanted in a patient's stomach.
FIG. 1B is an enlarged view of a portion of the system of FIG. 1A.

Referring to FIGS. 1A and 1B, a stimulator 10 in accordance with the invention is illustrated as it is implanted in a stomach 100. The stimulator 10 is implanted through a patient's mouth 101, pharynx 102, esophagus 103, and then into the stomach 100 using endoscopic instrument 110. A surgical placement method and stimulator are described in U.S. Pat. No. 6,535,764 incorporated herein by reference. Alternative stimulator attachment mechanisms and surgical implanting techniques are contemplated, including but not limited to the stimulators and implanting techniques described with reference to U.S. application Ser. Nos. 10/109,296 and 10/116,481.

Figure 3:
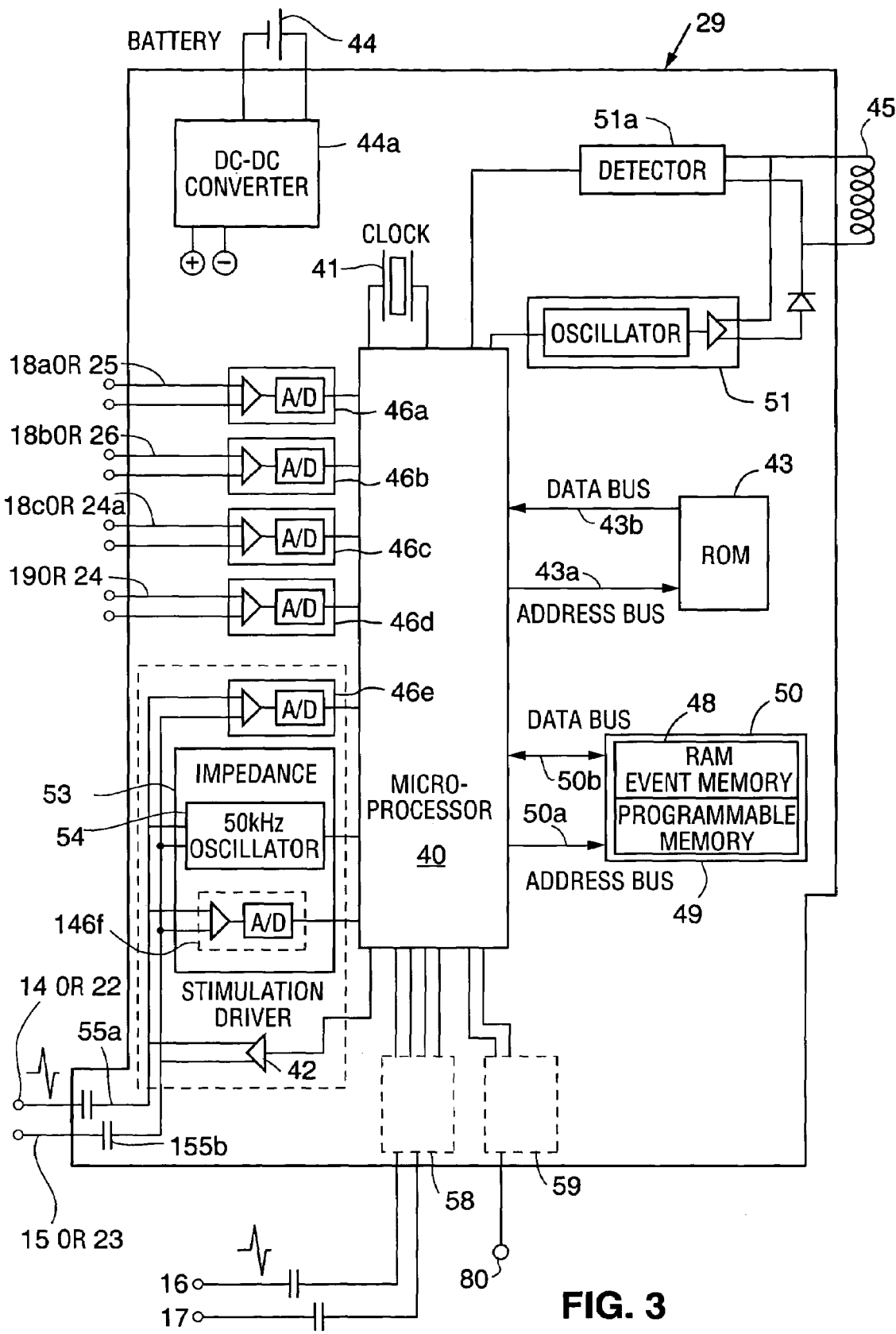
FIG. 3 is a schematic diagram of the circuit of an electronic stimulator of the present invention.

The stimulator 10 comprises an electronics housing 11 attached to the inside of a stomach 100 and containing the stimulator electronic circuitry 29 (FIG. 3). Leads 12, 13 are coupled to the electronics circuitry 29 and extend from the housing 11 to terminate in stimulating electrodes 14, 15 respectively that are attached to the stomach wall. The housing 11 and the electrodes 14, 15 may be attached at a variety of locations within or on the stomach, including but not limited to either on the greater curvature or the lesser curvature, or at the fundus or the antrum. It is also contemplated that a plurality of electrode pairs may be implanted at various locations in or on the stomach 100. The electrodes may be affixed by separate anchor or otherwise electrically coupled to the stomach wall.

The housing 11 includes electronic circuitry 29. As shown in FIG. 3, the electronic circuitry 29 of the stimulator 10 also includes a telemetry circuit for communication with separate devices.

The electronic circuitry 29 receives sensing information; provides stimulating electronic pulses through the electrodes 14, 15 to the stomach wall; and telemetry communication with an external unit such as a reader, recorder or controller. The stimulator 10 may be in communication with the electronic circuit 29 as described herein or with a separate controller (e.g. controller 70 in an external device 60 as in FIG. 4), which controls the stimulator 10.

Lead wire 12 includes separate impedance electrodes 16, 17 electrically coupled to the electronic circuit 29 by way of separate electrical connectors extending along lead wire 12. The impedance electrodes 16, 17 are positioned to sense the impedance of contents of food in the stomach when they are interrogated. The impedance of the contents provides information on the food or liquid that has been ingested. For example, fat typically has higher impedance than carbohydrates. The impedance electrodes may be interrogated by the controller 40 (FIG. 3) or controller 70, after there is an indication that food has been ingested. Such indicators may include, for example, change in temperature, change in pH, change in stomach contractions, and change in pressure, as described herein. The impedance sensors may also be interrogated on a periodic basis. Thus, sensing and power expenditure can be limited to the time at which the sensing is needed.

As illustrated in FIGS. 1A-1B, the housing 11 includes sensor 18a located on the housing and/or a sensor 18b extending from the housing 11. Alternatively or additionally, a sensor 18c may be located separately on the stomach wall and/or a sensor 19 may be otherwise positioned adjacent or coupled to the subject. Sensors 18a, 18b, 18c are located within or attached to the stomach wall. Sensor 18c may be attached to or otherwise coupled to or engaging the inside of the stomach wall, for example using a separate or integrally formed anchoring device, and may be introduced and attached to the stomach wall endoscopically or may be introduced and attached to the stomach laparoscopically.

Sensor 19 is coupled to the patient. In this illustration, the sensor 19 comprises a separately implanted device located subcutaneously within a patient's torso.

The sensors 18a-c, 19 may each comprise one or more sensors that provide feedback on a condition of a patient or information relating to the gastro-intestinal system of the patient. For example, the sensor may comprise an accelerometer that detects patient gross movement and/or respiratory movement from which patient state of wakefulness may be determined. The sensor 18a-c, or 19 may be coupled to the electronic circuitry 29 or to another control device by, leads to the electronic circuitry 29 or other control device or by telemetric or other communication modes.

The sensors 18a, 18b, and 18c are positioned to directly sense information concerning the stomach. The sensors 18a-c may include, but are not limited to one or more of the following: temperature sensors, contraction sensors, pressure sensors, strain gauges, pH sensors, accelerometers, optical sensors. As noted above, the sensors 18a-c are electrically coupled to, or are otherwise in communication with the electronic circuitry 29. (Alternatively they may be in communication with a separate or external controller, e.g., controller 70, that controls the stimulation pulses in response to information sensed by one or more of the sensors.)

The stimulator 10 comprises an anchor 123 and housing 11. The anchor 123 comprises an elongate member 124 having and expandable distal end 125 and a stimulating electrode 126 in the form of a ring of a corrosion resistant metal conductor. The stimulating electrode may be used instead of or in addition to one of electrodes 14, 15. A strain gauge 121 is included on the elongate member 124 and is electrically coupled through housing 11 to electronic circuitry 29. The strain gauge 121 is located adjacent electrode 126 on the anchor 123, which acts to anchor the electrode in the stomach wall. The strain gauge acts as a contraction sensor as described herein. Construction of and implanting techniques for such stimulator, for example, are described in U.S. Pat. No. 6,535,764 incorporated herein by reference. The electronic circuitry 29 provides sensing, stimulating electronic pulses through the electrodes to the stomach wall, and telemetry communication with an external unit such as a reader, recorder or controller.

Figure 2:
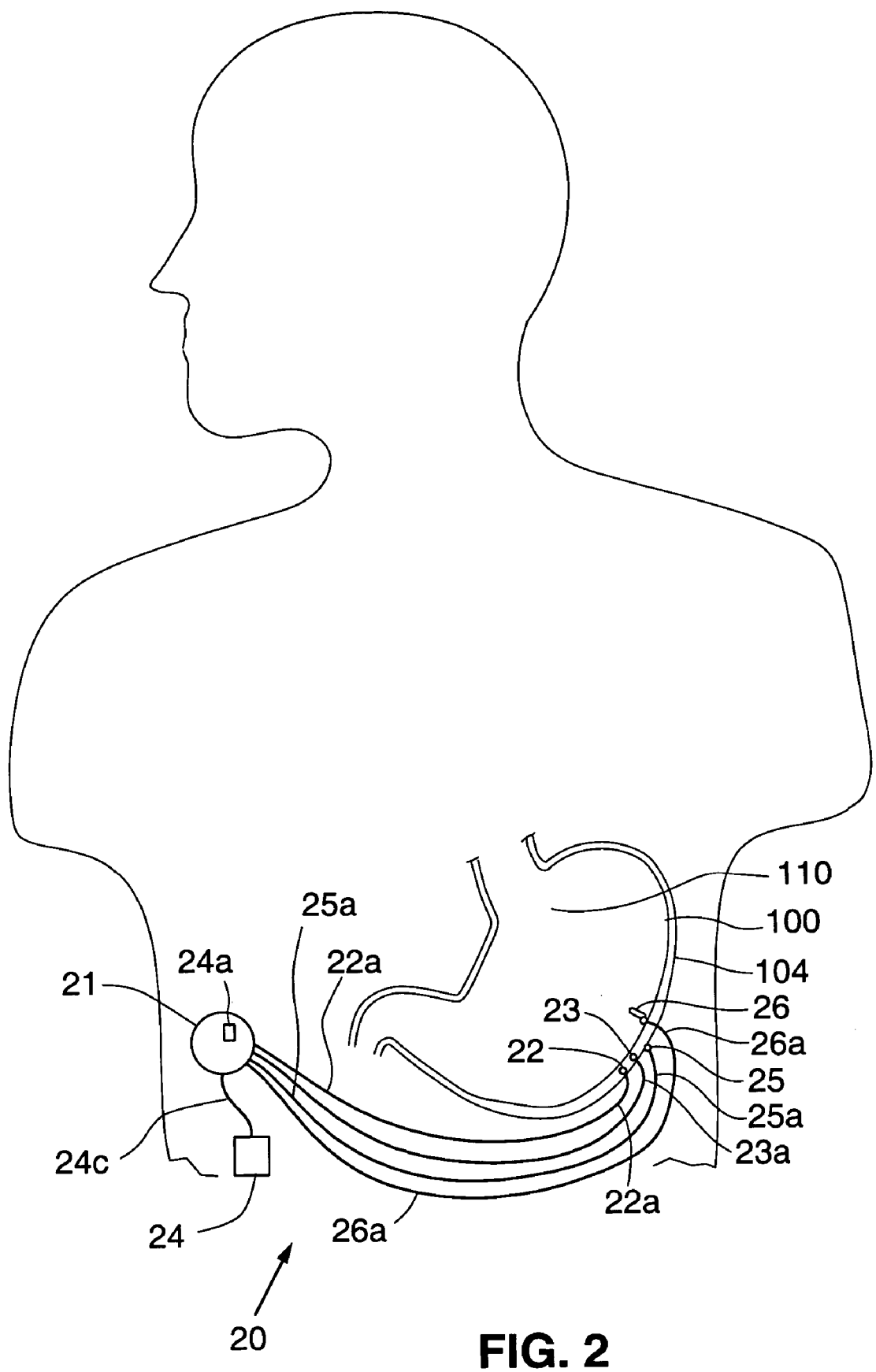
FIG. 2 is a schematic view, illustrating an embodiment of a stimulator according to the invention implanted in a patient.

FIG. 2 illustrates an alternative configuration of a stimulator in accordance with the invention. The stimulator 20 comprises a housing 21 implanted subcutaneously within a patient. The stimulator further comprises leads 22a, 23a extending from the housing 21 through the abdomen and to the stomach 100 where electrodes 22, 23 at the end of the leads 22a, 23a are implanted into the stomach muscle layer from the outside of the stomach 100. A method of implanting the stimulator housing 21 and laparoscopically implanting the electrodes 22, 23 in the stomach 100 is generally known to those of ordinary skill in the art.

The housing 21 further comprises a sensor 24a located on the housing 21 and/or a sensor 24b located elsewhere in the patient and coupled to the electronic circuitry 29 (FIG. 3) in the housing 21 by lead 24c. The sensor 24a or 24b may, for example, include an accelerometer that is configured to sense motion of the patient. The stimulator also includes sensors 25, 26, that are implanted on and in the stomach 100, respectively, with leads 25a, 26a extending from the sensors 25, 26 to the housing 21. Sensor 26 is exposed to the inside of the stomach 100 while sensor 25 is attached to the outside of the stomach. Leads 22a, 23a and 24c, 25a, 26a are electrically coupled to the electronic circuitry 29 located in the housing 21. When the sensors 25, 26 are implanted in the stomach, they may sense presence of material in the stomach, composition of such material and temperature, pH or pressure within the stomach, and/or patient motion corresponding to respiration or gross movement. Sensors positioned on the stomach may also sense various parameters that indicate the actions of the stomach, e.g., movement, contractions. The sensors positioned on the stomach may also utilize various imaging techniques, e.g., ultrasound, and light, to identify presence or composition of food or material in the stomach.

In use, once the stimulator (e.g., 10, or 20) is deployed electrical stimulation is provided through electronic circuitry 29. The electronic circuitry 29 is capable of producing various types of programmable waveforms that provide stimulation to the smooth muscle lining of the intestinal tract. It is well known to those of ordinary skill in the art, there are many different types of electrical stimulation programs and strategies which can be utilized for providing electrical stimulation parameters through the circuitry 29, the principal focus being providing electrically stimulating parameters for the stomach. In one embodiment the focus of the electrical stimulation is to cause gastric retention of food to produce a sensation of satiety. Another focus of the electrical stimulation may be to interfere with the innate peristalsis of the stomach, which is intended herein to mean to movement of the stomach that typically also acts to break down food and/or moves material towards the antrum or out of the stomach. Another focus is to cause a sensation of satiety by stimulating the stomach. Another focus is to control the secretions relating to the stomach or hunger by stimulating the stomach.

An embodiment of the electronic circuitry 29 is illustrated in FIG. 3. The electronic circuitry 29 of the stimulator is located in the housing 11. The electronic circuitry 29 may be in a form of a standardized chip that may be used with one or a variety of sensors, including but not limited to those described herein. The electronic circuitry 29 or similar electronic circuitry may also be included with separately implanted sensors or components of the system. Thus the various components may be configured to communicate with the other components through telemetry or similar signaling.

The circuitry 29 comprises, a microprocessor or controller 40 for controlling the operations of the electronic circuitry 29, an internal clock 41, and battery device 44 such as a pair of lithium iodine batteries for powering the various components of the circuit 29. As such, the controller 40 and battery device 44 are coupled to each of the major components of the circuit as would be apparent to one of ordinary skill in the art. The battery 44 has its output supplied to a DC-to-C converter 44a to provide a higher voltage, which is utilized for electrical stimulation pulses. The DC-to-DC converter 144a is conventional and provides an output voltage desired for stimulation. The internal clock 41 may also include a real time clock component that communicates with the microprocessor 40. The real time clock component may be used to control stimulation, e.g. by stimulating or allowing stimulation only at a particular time of the day. The real time clock component may also provide a date/time stamp for detected events that are stored as information in a memory device. The memory may be preserved by only saving information corresponding to an event of interest which is saved along with the time/date when the event occurred.

The controller 40 is coupled to stimulation driver 42, which is coupled to stimulating electrodes (e.g., 14, 15, 22, 23) that are used to provide electrical stimulation in accordance with programmed parameters, including in response to sensing conditions relating to the patient or the patient's intake of food as described herein.

The controller 40 is coupled to ROM 43, which contains the program instructions for the controller 40 and any other permanently stored information that allows the microprocessor/controller 40 to operate. The controller 40 addresses memory in ROM 43 through address bus 43a and the ROM 43 provides the stored program instruction to the controller 40 via data bus 43b. The controller 40 controls the telemetry coil 45, which communicates with an external control or programming device 60 (FIG. 4), e.g., via a modulated RF signal. Processor 40 is coupled to a buffered oscillator 51 that provides an RF signal to be emitted from the telemetry coil 45. The RF signal is preferably at about 100 kHz-5 Mhz so that the signal is efficiently transmitted through tissue. The controller 40 controls the oscillator 51 and provides data to be modulated with the RF signal. For example, various sensed data such as motion, transmitted or reflected light parameters, pressure, pH, temperature, local muscle contraction, strain, impedance, electrical activity (EMG) etc., may be delivered via a modulated signal through the telemetry coil 45. When the telemetry coil 45 is receiving an external telemetry signal, the buffered oscillator 51 is disabled. Telemetry signals received on the telemetry coil 45 are detected in a detector circuit 51a and communicated to controller 40. The detector circuit may be selected based on the modulation used for the telemetry signals.

The circuit 29 may also be coupled through A/D converters (with amplifiers) 46a, 46b, 46c, 46d to one or more sensors 18a-c and 19, or, 25, 26, 24a, 24, 121 respectively. The A/D converters convert a representative analog electrical signal from the sensors into a digital signal communicated to the controller 40. Suitable types of these sensors may include but are not limited to the types of sensor described herein. Such sensors at various locations are coupled to the electronic circuit by way of lead wires or through alternative means of communication such as telemetry, wireless communication or indirectly through a separate controller e.g., controller 70.

Controller 40 is coupled to RAM 50 via an address bus 50a for addressing a location in RAM 50 and a bi-directional data bus 50b for delivering information to and from RAM memory 50. The RAM memory 50 includes event memory 48 that temporarily stores data recorded by sensors 18a-c, 19, 24a, 24, 25, 26, or electrodes 14, 15; 16,17; or 23; 23. RAM memory 50 also includes a programmable memory 49 which may be programmed, for example, by an external programmer 60. The data stored in the programmable memory may include specifications for the electrical stimulation operating modes (e.g., waveform, type of stimulations: for pacing, inducing, interfering with or reversing contraction, for interfering with innate activity, for controlling biochemistry or secretions relating to the stomach, or other types of stimulation) and various procedures or responsive parameters (e.g., for turning on or off various sensing or stimulation functions, parameter modification, protocols or procedures for recognizing various conditions of the patient of the patient's gastrointestinal tract and protocols or procedures for responding to such recognition). These data and procedure/protocol elements, including responsive elements that respond to sensed data, may also be located in whole or in part in other controller devices that may be located independently from electronic circuitry 29. The programming may be done in response to sensed information or, it may be done automatically by an external controller or as desired by a treating physician, etc. Sensed data acquired from the sensors or electrodes, provided to the controller 40 may be stored in event memory 48 in the RAM 50. The data stored in the event memory 48 may be sent intermittently as data bursts via the telemetry coil 45, as opposed to continuously, in order to save battery power. The clock may also mark or date/time stamp the data stored in event memory. The processor also may select events based on predetermined thresholds or characteristics that are to be stored as a significant event, while other events are filtered out and not stored.

The electrodes 14, 15 or 22, 23 are coupled through A/D converters 46e and 46f to the microprocessor 40. A/D converter 46e converts the electrical EMG signal sensed by the electrodes 14, 15 or 22, 23 into a digital signal representative of the EMG electrical activity, which is delivered to the microprocessor/controller 40 and stored in the event memory 48 in the RAM 50. Also, the A/D converter 46f converts the electrical signal sensed by the electrodes 14, 15 or 22, 23 and provided through the impedance circuit 53 described below, into a digital signal representative of tissue impedance, which is delivered to the microprocessor and stored in the event memory 48 in the RAM 50.

The electrode 14, 15 or 22, 23 outputs are used to provide electrical stimulation delivered through the stimulation driver 42 to electrodes. The stimulation modes and parameters can either be set using the external programmer 60, or they may be set in response to sensory feedback. The same electrode outputs may be used to sense impedance of the stomach tissue or of the contents of the stomach depending upon the location of the electrodes. Impedance circuit 53 is used to sense impedance and EMG or other electrical activity information is provided to the processor 40 through A/D converter 46e. The electrodes 14, 15 or 22, 23 are coupled through coupling capacitors 55a and 55b respectively, to output of electrical stimulation driver 42 and input of A/D converters 46e, 46f.

The impedance circuit 53 comprises a constant current source oscillator 54 that oscillates at a frequency of 50-100 kHz, and A/D converter 46f with an output coupled to the controller 40. The oscillator 54 provides a constant current source through electrodes 14, 15 or 22, 23 resulting in a voltage across the electrodes 14, 15 or 22, 23 that is representative of impedance, in view of the constant current. The voltage is provided through and is converted by A/D converter 46f to a digital signal representative of impedance. A/D converter 46f has a bandwidth that includes the 50 kHz frequency signal while filtering out the electrical stimulation signal that is delivered to the electrodes 14, 15 or 22, 23 through electrical stimulation driver 42, and the EMG signal that is sensed by the electrodes 14, 15 or 22, 23. Both of the outputs are filtered out by A/D converter 46f. A/D converter 46e has a bandwidth that filters out the 50-100 kHz signal. Further, when a stimulation signal is being delivered, the controller 40 does not receive signals from A/D converters 46e and 46f. Thus the EMG and impedance sensing functions and the stimulation deliver functions may be separated through the electronic circuitry 29, though using the same electrodes.

An additional circuit 58 may be provided in the electronic circuitry 29 comprised of similar components configured like impedance circuit 53. The circuit 58 delivers an interrogating electrical pulse to the electrodes 16, 17 and senses impedance of material between the electrodes. The electrodes 16, 17 are positioned to be in electrical contact with contents of materials that may be in the stomach. As illustrated in FIGS. 1A-1B, the electrodes 16, 17 are located on separate leads along lead wires connecting the electrodes 14, 15 to the stimulator housing 11. An A/D converter coupled to the controller 40 converts the sensed information into a representative signal communicated to the controller 40.

Additional stimulating sensing electrodes and corresponding signal processing circuits may also be provided.

Figure 4:
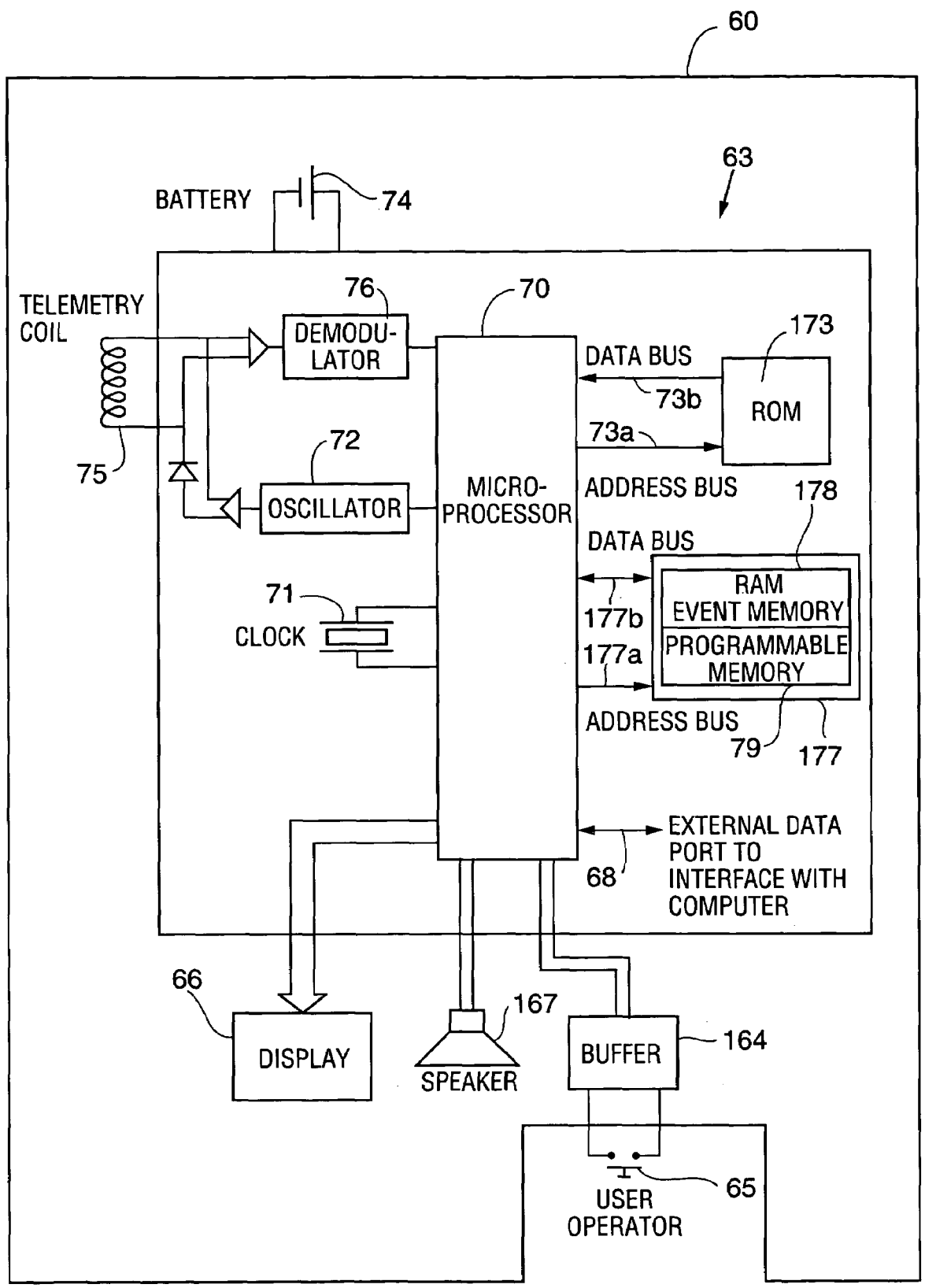
FIG. 4 is a schematic diagram of the circuit of an external programmer/recorder of the present invention.

FIG. 4 illustrates the electronic circuitry 63 for external programmer 60. The electronic circuitry 63 comprises: a microprocessor or controller 70 for controlling the operations of the electronic circuitry, an internal clock 71, and a power source 74 such as battery device for powering the various components of the circuit 63. As such, the controller 70 and battery device 74 are coupled to each of the major components of the circuit as would be apparent to one of ordinary skill in the art. The controller 70 is coupled to a speaker 67 that provides audible alerts and a display 66 such as a CRT to display data such as recorded data, sensed parameters, treatment parameters and status of device (e.g. position or battery charge status). The controller 70 is coupled through a buffer 64 to external input device 65 that is used to provide program parameter input, e.g. from a user, for a user to request data displayed in a desired format through display 66 or speaker 67, or to turn device on and off. The external programmer 60 is also provided with an external data port 68 to interface with a computer and provide a means for bi-directional communication of data or commands. The computer may provide programming or data to the controller/microprocessor 70. A user may also interface with the computer to provide treatment protocols or changes in protocols, etc. Also, a user may control the turning on and off of the stimulation program.

The controller 70 is coupled to ROM 73, which contains the program instructions for the controller 70 and any other permanently stored information that allows the microprocessor/controller to operate. The controller 70 addresses memory in ROM 73 through address bus 73a and the ROM 73 provides the stored program instruction to the controller 70 via data bus 73b. The controller 70 controls the telemetry coil 75, which communicates with stimulator electronics 29 (FIG. 3) through its telemetry coil 45. Controller 70 is coupled to an oscillator 72 that provides an RF signal, preferably having a characteristic frequency of 500 kHz or higher, to be emitted from the telemetry coil 75. The controller 70 controls the oscillator 72 and provides data to be modulated with the RF signal, for example, programming information, stimulation parameters, etc. The telemetry coil 75 also receives information transmitted via RF signal from telemetry coil 45 on the stimulator 10 such as various sensed data, e.g., temperature, pressure, pH, impedance of the stomach or of its contents, optical characteristics of stomach contents, motion data, electrical activity (EMG), etc. The received RF signal is passed through A/D converter 76 and is transmitted to the controller 70. The data is delivered to the event memory 78 in RAM 77 by way of data bus 77b for temporary storage. The data may be retrieved from RAM 77 by addressing the storage location via the address bus 77a.

Event memory 78 temporarily stores data sensed by sensors 18a-c, 19, 24a, 24, 25, 26, 121 or electrodes 14, 15, 16, 17, 22, 23; recorded through controller 40; and delivered via telemetry to the external programmer 60. The data may then be downloaded onto a computer using the external data port 68. The RAM 77 also includes a programmable memory 79 which may be programmed, for example, to specify operating modes such as waveform, frequency, pulse width, amplitude, repetition rate, etc. which programming is then telemetrically communicated to the stimulation device 10, 20. The modes and parameters can either be set using an external programmer 60 and/or set in response to sensory feedback according to programs.

The stimulator 10 or 20 may be programmed to deliver electrical stimulation in response to sensed parameters. The sensors 18a-c, 19, 24a 24, 25, 26, 121 or electrodes 14, 15, 16, 17, 22, 23, depending upon their specific location, may comprise (but are not limited to): a temperature sensor that may sense a change in temperature or a rate of change in temperature that indicates ingestion of food or liquid; a pH sensor that may be used to determine when food has been ingested; an optical emitter/sensor that may be used to determine the presence and/or composition of food; a pressure sensors that may be used to sense motility patterns, e.g. presence, strength or frequency of contractions; a contractions sensor that may provide information on stomach contractions an local responses to stimulation; an impedance sensor that may provide information on the content of the stomach and/or an impedance sensor that may determine when a characteristic EMG pattern exists to determine wakefulness of a subject; a motion sensor that determines an activity level or wakefulness of a subject; a biochemical sensor that provide information on biochemical compositions relating to the stomach such as secretions.

The responsive devices may comprise at least one sensor and at least one responsive element. From sensed information, the responsive element determines the existence of a condition, e.g., presence of food; ingestion of food; type of food ingested; activity level of a subject; wakefulness of a subject; time of a daily cycle or schedule; contractions of the stomach, etc.

The responsive element may combine a number of sensed parameters to determine the existence of a condition or circumstance or a probability of the existence of a condition or circumstance. The responsive element may thereupon determine a course of treatment, including protocols, stimulation parameters and whether or not to stimulate. In one variation responsive element may respond by stimulating to interfere with the stomach contractions; to slow, stop or reverse the innate peristaltic contractions that tend to move food through the stomach.

For example, the combined determination of temperature changes indicating likelihood of food ingestion, and an accelerometer indicating that a subject is not sleeping or is not highly active may trigger a responsive element to stimulate the stomach to retain food for a predetermined period of time. The accelerometer can determine a low level of activity indicating likelihood of a sleep state, but may be overridden by a temperature sensor sensing that food has been ingested and thus requiring stimulation. PH may be used in a similar manner as temperature to indicate a likelihood of food ingestion. A timer may also confirm the likelihood that food is being eaten given the time of day, or may refrain from stimulating in spite of food being ingested if it is a certain time of day, e.g., when the stomach is naturally cleaning out the stomach as it typically does during the night.

The responsive element may receive input from one or more sensors and, in response, the responsive element may interrogate another sensor for information to determine a course of action. This may be used to save battery or power consumption. This may also be used to confirm the existence of a condition or circumstance using more than one sensor. For example, one or more sensors may provide information that food has been ingested. Upon making this determination, another sensor may be triggered to determine what type of food has been ingested. For example, an impedance sensor may determine characteristics of the content of the stomach by measuring the impedance of the contents of the stomach. An optical emitter/sensor may sense the light reflectance/transmission characteristics of contents of the stomach. This information may be recorded in a memory device and downloaded. Also the information may elicit a simulation response controlled by the responsive element when a certain type of food is detected. In addition foods may be provided as part of an eating regimen that have markers for different types of food. Gastric retention of some foods may be created while permitting movement of others out of the stomach.

Figure 5:
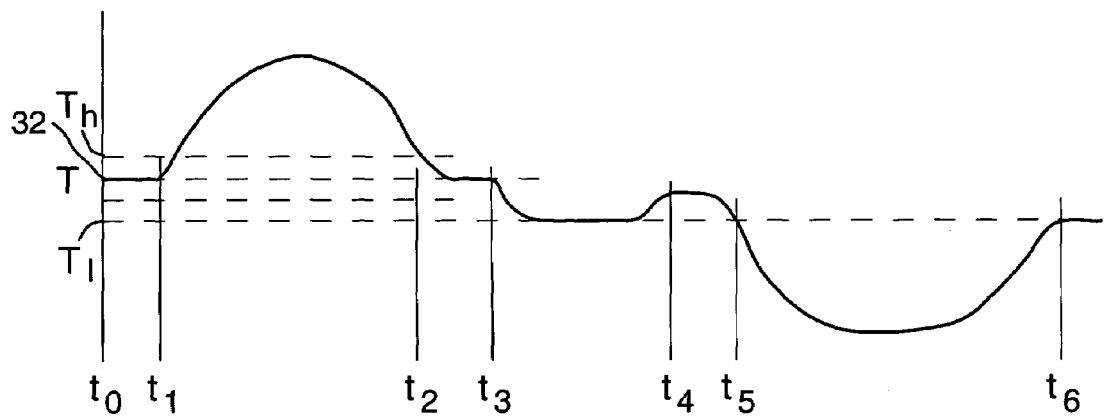
FIG. 5 is an exemplary signal sensed by a temperature sensor over a period of time.

FIG. 5 illustrates an exemplary processed temperature signal sensed by a temperature sensor over a period of time. The temperature sensor is positioned in the stomach to sense temperature or temperature changes that may occur due to a subject ingesting material such as food or liquid. Sensors 18a, 18b, 18c, or 26 may be suitable as temperature sensors that are positioned within the stomach.

As illustrated in the exemplary sensed signal in FIG. 5, temperature is on the y-axis while time is on the x-axis. From time $t_0$ to $t_1$, the temperature sensed is relatively constant, at core body temperature of about 37 degrees Celsius. Between time $t_1$ to $t_2$, warm food is ingested by a patient and the sensor senses a characteristic temperature over time as indicated by the temperature signal from time $t_1$ to $t_2$. From time $t_2$ to $t_3$, temperature has again returned to normal. From time $t_3$ to $t_4$, temperature changes much more gradually and to a lesser degree than from time $t_1$ to $t_2$. This temperature fluctuation does not meet a temperature threshold $T_h$ (high) or $T_1$ (low). The absolute change in temperature and the rate of change in temperature are also less than the absolute or rate of change in temperature from time $t_1$ to $t_2$. From time $t_4$ to $t_5$, the temperature is again approximately normal at 37 degrees Celsius. From time $t_5$ to $t_6$ cold substance is ingested by a patient and the sensor senses a characteristic temperature over time as indicated by the temperature signal from time $t_5$ to $t_6$.

The signal is processed either by controller 40 or is telemetrically transmitted by electronic circuit 29 to external programmer 60. The controller 40 or controller 70 may process the signal in a variety of ways to determine whether the characteristic signal in a period of time indicates that food or other material has been ingested. For example, from the sensed temperature signal, a change in temperature over time for the signal or absolute change in temperature may be derived or determined. If the change is substantially fast and of a significant degree, it determines that food or a substance has been ingested. Thus, using one or more temperature parameters, e.g., actual temperature sensed, change in temperature or rate of temperature change, a determination may be made that a subject has ingested material. Additionally, or alternatively other characteristics of a sensed temperature signal may be observed to conclude that the signal is characteristic of ingestion of material, ingestion of a certain type of material (e.g., liquid or food), or of a threshold amount of material. For example, the sensed signal may be compared to a characteristic signal a comparison from which, a requisite amount of or degree of correlation with a characteristic material ingesting signal may cause the processor to conclude that a requisite amount of food has been ingested. A responsive element then responds either by stimulating or not stimulating the stomach, by increasing, decreasing stimulation or by altering stimulation parameters.

Figure 6A:
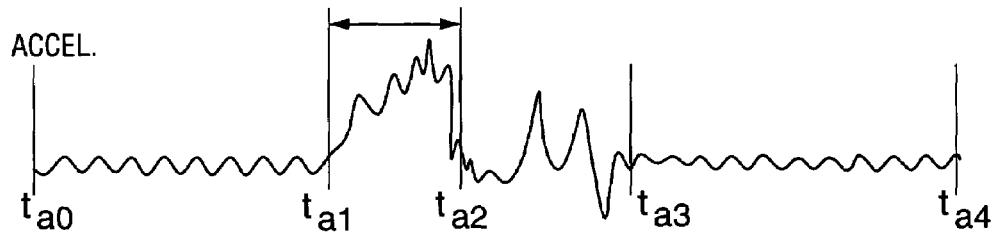
FIG. 6A is an exemplary signal sensed by an accelerometer over a period of time.
Figure 6B:
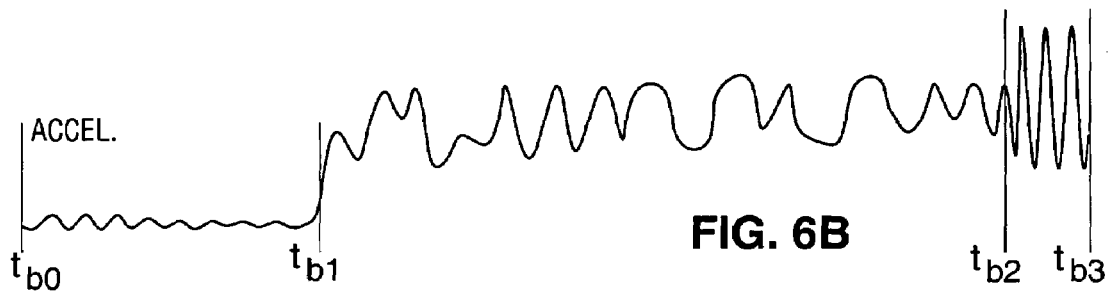
FIG. 6B is an exemplary signal sensed by an accelerometer over a period of time.

FIGS. 6A and 6B illustrate schematic exemplary accelerometer signals from one axis of a multi axis accelerometer The y-axis corresponds to detected motion while the x-axis represents time. Referring to FIG. 6A, between time $t_{a0}$ to $t_{a1}$, activity is minimal showing characteristic movement corresponding to sleeping and respiration during sleeping. During this period, stimulation is turned off. From time $t_{a1}$ to $t_{a2}$, a burst in activity is sensed and then again from between $t_{a2}$ and $t_{a3}$. From time $t_{a3}$ to $t_{a4}$, the signal returns to the characteristic sleep and sleep respiration pattern. In this exemplary signal, the bursts in activity correspond to gross movement that may occur during sleep. This may be determined among other ways, by observing the movement returning to a typical sleeping pattern a short time after the gross movement occurs. The controller 40 of the electronic circuitry 29 or (or other controller or processor to which sensed data is supplied) is programmed to recognize the sleeping respiration movement and gross movements that correspond to movement during sleep. The program may compare a number of signal parameters and find a certain degree of correlation from which a determination of a condition is made. Such conditions may include for example, sleeping, resting but not sleeping, gross movement during sleep, or an exertion level. For example the sleep respiration pattern may include a respiration rate or pattern corresponding to sleep. If the gross movements are relatively short and the signal returns to the sleep respiration pattern, then the controller may be programmed to recognize the gross movement as "gross movement during sleep". If the movement is fairly rapid and at relatively higher amplitude, the controller may be programmed to determine that a higher exertion level exists.

Referring to FIG. 6B, between the time $t_{b0}$ to $t_{b1}$, activity is minimal and characteristic of sleeping. During this period, stimulation is turned off. From time $t_{b1}$ to $t_{b2}$ a burst in activity is sensed and again from time $t_{b2}$ to $t_{b3}$ gross movement is sensed. The movement from time $t_{b1}$ to $t_{b2}$, and from time $t_{b2}$ to $t_{b3}$ is characteristic of movement during wakefulness. The signal does not return to a characteristic sleep movement pattern. The controller is programmed to recognize this gross movement or continuation of such gross movement for a period of time as activity during a waking state. The controller may also compare the gross movement and detected respiration from movement of the chest to confirm the determination of the state of wakefulness of a subject. The movement from time $t_{b2}$ to $t_{b3}$ is more rapid and of greater magnitude indicating a greater level of exertion. The controller or processor processing the signal may, for example, recognize the activity level as a high level of exertion if the activity continues for a significant amount of time. The controller may accordingly then control the signal to turn the signal off during the period of high exertion. The controller may be programmed to recognize a number of parameters of the accelerometer curve including rate of change in motion, amplitude of motion signal and other types of motion having characteristic signals.

In addition to characteristics such as the ingestion of food being factored into a programmed device response, innate characteristics of the stomach may be sensed and used to make decisions relating to or to control or modify stimulation. For example, innate stomach contractions may be observed periodically. Without food intake, if the contractions increase, it may be determined that the subject is getting hungry or will be getting hungry. The responsive device may be programmed to respond to such an indicative contraction pattern by controlling the stomach contractions, for example, by interfering with the contractions. Alternatively or additionally, a biochemical sensor may be used to identify the presence, absence or quantity/concentration of a biochemical substance such as a hormone related to hunger (e.g. ghrelin), or another stomach secretion such as an enzyme or acidic composition. The responsive device may respond to the information by stimulating. The information may also be stored and communicated to an external device or downloaded at a later time to enable the subject to otherwise respond or to observe subject patterns over time.

Figure 7:
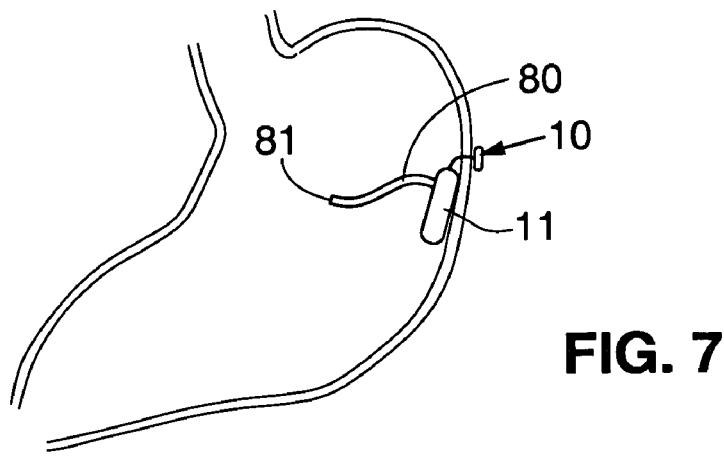
FIG. 7 is a stimulator with an optical sensor according to the invention.

Referring to FIG. 7 an optical sensor 80 is illustrated extending from the housing 11 of the stimulator 10 within the stomach. The optical sensor 80 includes a distal end 81 configured to illuminate and sense the optical characteristics of food or other material within the stomach. The optical sensor 80 uses spectroscopy by detecting light absorption, reflectance or excitation characteristics that correspond to various compositions of materials in the stomach.

According to one embodiment of the invention, the sensor light source emits and detects light or absence of light of certain wavelengths. According to this embodiment, the sensor 80 includes at least one light source, e.g. an LED or optical fiber source that emits either a white light or light of one or more particular wavelengths. The light source 84 is controlled by the controller, which directs a brief pulse of light into the intestinal tract or at the contents of the stomach. The sensor 80 further includes at least one sensor for sensing reflected or transmitted light. The reflected or transmitted light indicates particular reflectance or absorption of certain wavelengths of light characteristic of certain materials or substances. The excitation characteristics of the object and/or the absorption of a particular wavelength (non-reflectance) of light to which a photo diode is sensitive is determined when the photo diode senses or does not sense a sufficient amount of light corresponding to a particular wavelength. The sensor 80 is coupled to the processor 40 through processing circuit 59 (FIG. 3). The processing circuit 59 energizes the optical fibers or LED's upon receiving instructions from the processor 40. The processor circuit 59 also receives signals from the light sensing portions of the sensor corresponding to sensing reflected or transmitted light and converts the signals into a digital signal that is communicated to the processor 40. The processor 40 or processor 70 receiving related data from the electronic circuitry 29, determines whether or not certain materials or compositions are present based on the sensed reflected or transmitted light.

In response to sensing presence of food of a particular composition, the device may do one of several things. For example, the device may stimulate the stomach to retain the food based on the detected food composition. The device may stimulate the stomach to provide a sensation of satiety or a slightly uncomfortable sensation if a substance is detected that is not part of a pre-approved eating regimen, e.g., a fat, carbohydrate or type of carbohydrate (e.g., simple or complex).

In one embodiment, pre-approved food are produced with a marker a, e.g., a fluorescing marker. If an unapproved food is eaten, the device responds by stimulating the stomach to create an unpleasant sensation. Thus training the individual to dislike the unapproved foods.

The optical sensor 80 may be interrogated by the controller 40 delivering a control signal to the processing circuit 59, which interrogates the sensor 80 to sense the contents of the stomach. In order to save device power, this control signal may be delivered only if ingestion of food is sensed, e.g. with a temperature sensor as described above. The sensor 80 in one embodiment is interrogated immediately after sensing ingestion of material so that the composition of the material may be sensed prior to initial breakdown of the material by digestive enzymes. The device may also record a log of sensed information for dietary tracking purposes that can be downloaded after a period of time.

Figure 8:
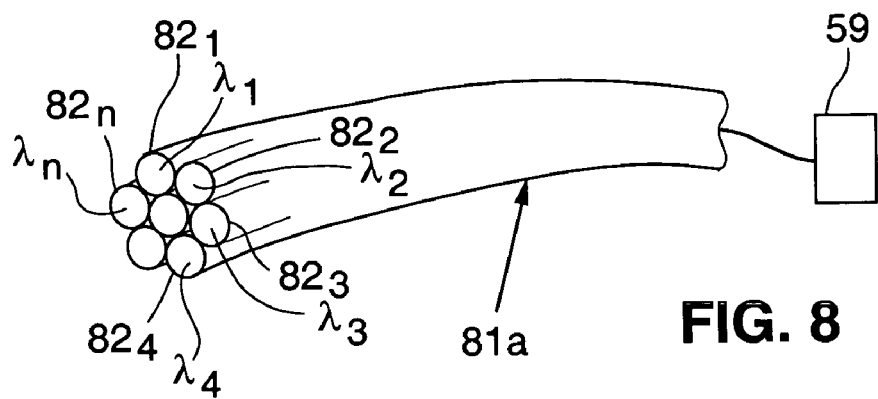
FIG. 8 is an enlarged perspective view of an alternative distal portion the optical sensor shown in FIG. 7.

Referring to FIG. 8, one variation 81a of a distal end 81 of the optical sensor 80 is illustrated. The variation 81a of the distal end comprises light emitter detectors $82_{1-n}$, each of the emitter/detectors $82_{1-n}$ comprising light fibers and light sensors (e.g. photodiodes) emitting and detecting particular corresponding wavelengths of light $\lambda_{1-n}$ (where n is a positive integer). The emitter/detectors $82_{1-n}$ may alternatively comprise LED's and light sensors. The emitter/detectors $82_{1-n}$ illuminate the contents of the stomach and then detect the resulting reflectance of light or the excitation characteristics of the contents of the stomach for the particular wavelengths of light $\lambda_{1-n}$. The sensed light is converted to a representative signal by processing circuit 59, which processes sensing light information in a manner that would be apparent to one of ordinary skill in the art.

Figure 9:
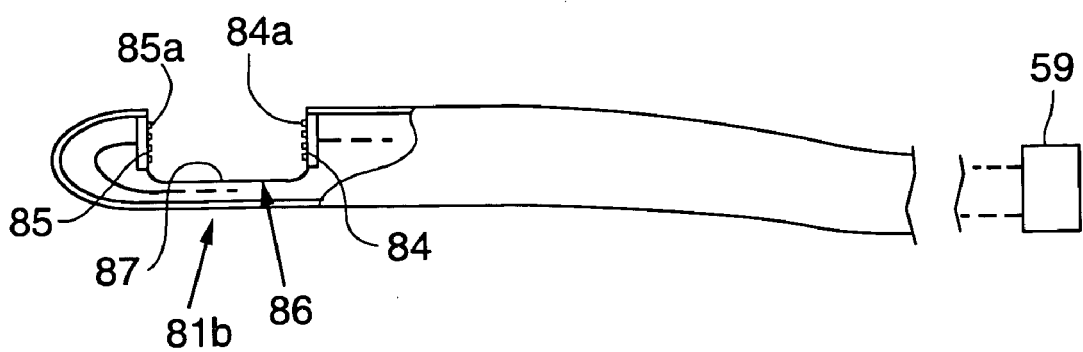
FIG. 9 is an enlarged perspective view of an alternative distal portion the optical sensor shown in FIG. 7.

Referring to FIG. 9 a variation 81*b* of the distal end 81 of the optical sensor 80 is illustrated. The variation 81*b* of the distal end 81 comprises a concave portion 86 forming an opening 87 for temporarily receiving a portion of the contents of the stomach 100. The opening 87 includes a proximal end 84*a* and a distal end 85*a*. This variation 81*b* of the distal end 81 comprises photo diode detectors 85 located on the concave portion 86 at the distal end 85*a* of the opening, and LED light source 84 on the concave portion 86 at the proximal end 84*a* of the opening 87. In this embodiment a white light source is used. The light source 84 and the photo diode detectors 85 are arranged with respect to each other such that light emitted from the light source 84 is received and sensed by the photo diode detectors 85. The photo diode detectors 85 may comprise an array of detectors or filters, each sensing a particular wavelength or range of wavelengths of light. Alternatively, a plurality of LED emitters of predetermined wavelengths (e.g. with filters) may be used to illuminate the stomach. Absorption of particular wavelengths may be used to determine presence or absence of various compounds.

The array of detectors is coupled to the processing circuit 59, which is coupled to the processor 40. The processing circuit 59 is configured to select the sensors or filters that correspond to wavelength(s) to be detected, e.g., based on a selected diagnostic mode. The processor 40 may select a particular substance or food, etc. for which to sense. This may be preprogrammed into the processor 40 or may be modified during the course of treatment or diagnosis with the stimulator system. The processor 40 instructs the processing circuit 59 to cause emission of light and then sense light transmitted through material located within the opening 87.

In use, food or other material in the stomach is accumulated in the opening 87 through which light is transmitted. The photo diode sensors 86 sense light that is transmitted through the food or material in the opening 87. The photo diode detectors 85 are selected to detect different wavelengths of light. The food has a characteristic light absorption that can be used to identify the composition of the food. The light characteristics of the stomach tissue and corresponding light absorption or reflectance signal can be filtered out of the signal leaving a signal corresponding to the contents of the stomach. The resulting sensed light signal is processed by the processing circuit 59, which transmits a representative digital signal to the processor 40 corresponding to the transmitted light sensed by the photo diode detectors 85.

As described above, the electronics circuit 29 is configured to receive sensed signal(s) indicative of optical parameter(s) such as one in which presence of certain foods is indicated. The sensed signal is communicated to the processor 40, which communicates a signal representative of the sensed information via the telemetry coil 45 to an external controller/processor 70. The information may, for example, be in the form of a composite signal combining sensed light information of each of the sensors, or may be temporally spaced signals for each of the sensors.

In another embodiment the device senses contraction by sensing pressure. The pressure within the stomach generally increases with an increased rate of contraction. For example, a pressure of about 250-300 mm Mercury indicates a level of contractions corresponding to a higher level of stomach activity that would be beneficial to suppress in order to control hunger. If the patient is in a state in which appetite is to be suppressed, then upon sensing contractions, the stomach is stimulated to reduce the contraction and thereby reduce hunger pangs. The pressure sensor may be located in the stomach such as sensor 18*a*, 18*b*, or 26. The pressure sensor may be located within the housing where the housing is constructed having a sufficiently thin wall to permit pressure changes to be sensed within the housing.

In another embodiment, a contractions sensor is positioned in or on the stomach wall such as sensors 18*a*, 18*b*, 18*c*, 25 or 26, 121 and senses stomach contractions. In response to sensing contractions, a responsive element may cause the stomach to be stimulated to manipulate the stomach contractions, e.g., by reducing or reversing the contractions.

During sleep, the stomach goes through a cleaning process. This process can be observed by pressure changes and emg signals characteristic of a sleep cycle. Accordingly, stomach emg can be monitored and stimulation can be prevented when such signal is present. Other indicators of sleep such as from an accelerometer can be used to confirm the sleeping state of the subject.

A real time clock may also be used to determine the times to stimulate or to not stimulate, e.g., on a daily schedule. For example a real time clock may in combination with a sleep sensor determine when to turn off stimulation, e.g. when the subject is supposed to be sleeping and when the parameters sensed indicate that the patient in fact is sleeping. The stimulation may be turned off a certain meal times to allow the subject to eat without interference of the peristaltic signals and to permit normal digestion of food.

The invention has been described with reference to preferred embodiments and in particular to a gastric stimulator, the present invention contemplates that a number of combination of sensors may be used to determine the state of a patient or the gastrointestinal tract of the patient and to determine, if, when and how to stimulate the stomach in response. A number of different signal and information processing techniques may be used to arrive at a stimulation protocol or modification thereof. A number of different communication schemes may be used between, the sensor processors and stimulation electrodes. Also the means for powering the implanted portions of the device may also vary in accordance with various techniques and devices.

The responsive element or responsive device may include one or more components that are located together or separately. For example a signal processing component may be located in an implanted device and a controller for determining the existence of a particular condition may be located in a separate component directly or indirectly in communication with the signal processing component.

Figure 11A:
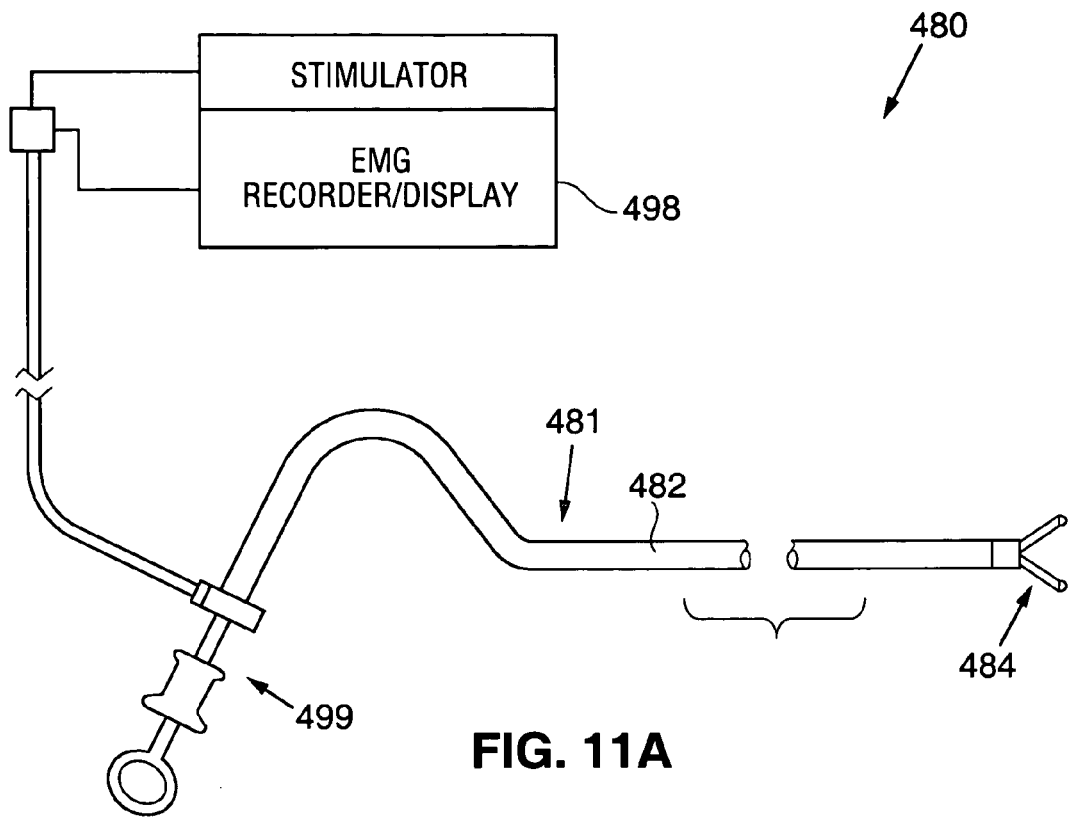
FIGS. 11A and 11B illustrate a device for optimizing electrical stimulation in the stomach.
Figure 11B:
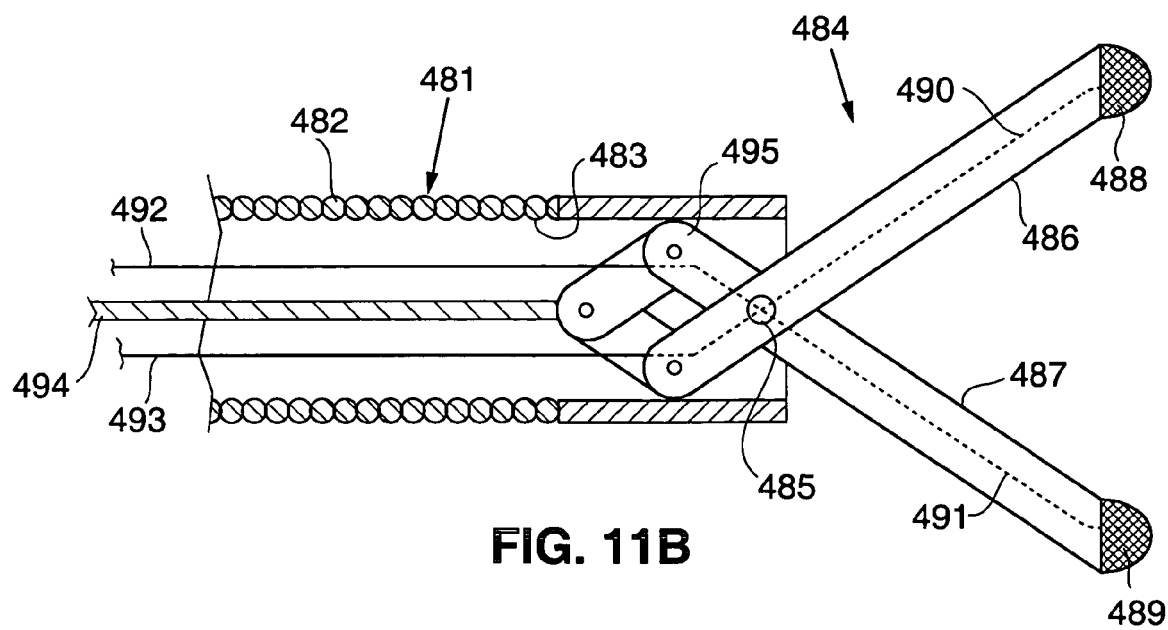

Other instruments and devices may be used to determine stimulation parameters locally at a stimulation site, in response to stimulation at a particular stimulation site. Referring to FIGS. 11A and 11B, an endoscopic instrument 480 is used to map electrical activity in the stomach wall and to identify and characterize the response of the stomach wall to various electrical stimulation parameters. The instrument 480 comprises an elongate flexible member 481 generally formed of a coil 482 with a lumen 483 extending therethrough. An end effector 484 is located at the distal end of the instrument 480. The end effector 484 comprises electrode members 486, 487 coupled together by a hinge 485. The electrode members 486, 487 include electrodes 488, 489 located at the ends of the members 486, 487. The electrodes 488, 489 are coupled through conductors 490, 491 extending through electrode members 486, 487 to wires 492, 493 which extend through the lumen 483 in the instrument 480 to a proximally located handle 499. The wires 492, 493 are coupled to an external stimulator/recorder unit 498, which supplies stimulation energy to electrodes 488, 489 through wires 492, 493 and records electrical activity sensed by the electrodes through the wires 492, 493. A mechanical wire 494 is coupled to a hinge actuating device 495 and extends through the lumen 483 to handle 499. The electrode members 486, 487 are initially in a closed position. When the wire 494 is moved distally using handle 499, the hinge actuating device 495 rotates the electrode members 486, 487 about hinge 485 to spread the electrode members 486, 487 and electrodes 488, 489 apart from each other. In this position (FIG. 11A-11B); the electrodes may be placed on the stomach wall at a desired site to measure and record electrical activity, electrical parameters, or to provide electrical stimulation pulses to the stomach wall. Upon providing stimulation pulses to the stomach wall, the response of the stomach (e.g., the presence, absence or degree of contraction) may be observed, either visually or through a sensor (not shown) located on the end effector 484 that senses muscle contractions, such as, for example, a strain gauge. The ideal location for attaching a stimulation device may be determined by sensing electrical activity, electrical parameters or by observing a location where stimulation results in a desired response. Also the ideal stimulation parameters or program may also be determined with the device by observing the response of a site to various stimulation parameters delivered by the end effector 484.

Figure 10:
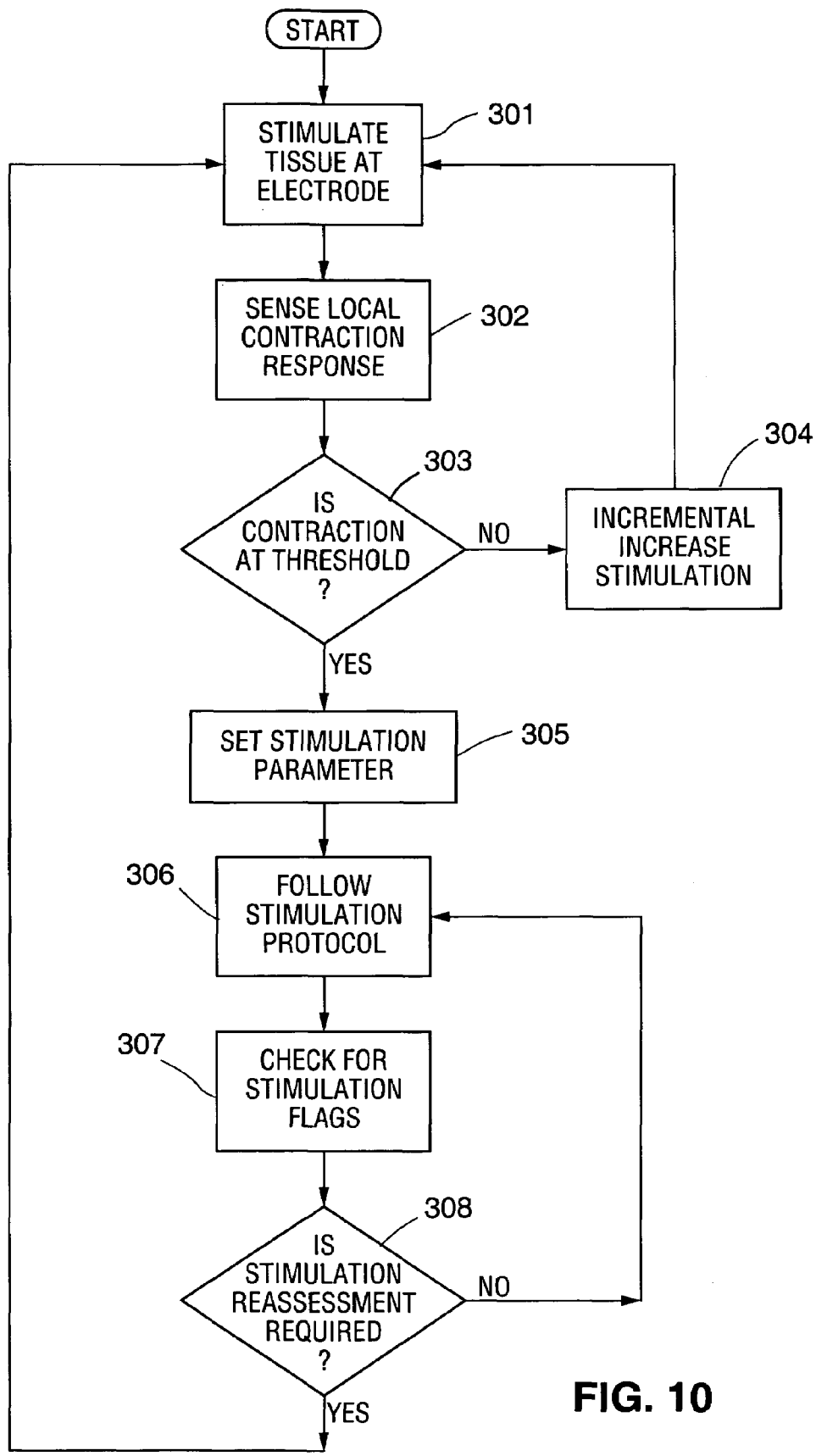
FIG. 10 is a flow diagram of a stimulation threshold determining device and method.

FIG. 10 is a flow chart illustrating operation of a stimulator according to one aspect of the invention. As is readily understood by one of ordinary skill in the art, the operation of the stimulator as set forth in FIG. 10 may be accomplished with readily recognizable structural elements, including, for example, a CPU or processor in conjunction with a program saved in a memory device. The stimulator first stimulated tissue 301 at a stimulation site. A local sensor in close proximity to the stimulation site senses a local contraction response at the stimulation site 302. If the contraction has not reached a suitable contraction threshold 303, e.g. preset or pre-programmed into the stimulator, the stimulation 301 and sensing 302 steps are repeated. If the contraction has reached a threshold 303, then the stimulation is set at the threshold or a preset amount above the threshold. 305. Stimulation then follows a protocol such as a protocol described herein where stimulation is provided under a certain set of circumstances and for a certain purpose, e.g., to control appetite 306. At a predetermined time, upon occurrence of a predetermined event, or at the request of a programmer, (e.g. through the external controller by a subject or provider), a check is made for flags indicating stimulation may need to be readjusted. 307. Such flags may include a preset passage of time, a occurrence of preprogrammed set of circumstances (e.g. based on algorithms defining the stimulation protocol or identifying circumstances that may indicate stimulation is not effectively being delivered). If the flags indicate stimulation reassessment is not required 308, the stimulator returns to step 306 wherein the stimulation protocol is again followed. If stimulation reassessment is required 308 then the stimulation step 301, the sensing step 302 and stimulation parameter setting step 305 are repeated as described above. The stimulator in accordance with the invention may include a plurality of electrodes and sensors that are independently tested and set for independently determined parameters.

While the invention has been described with reference to preferred embodiment, it will be understood that variations and modifications may be made within the scope of the following claims. Such modifications may include substituting elements or components that perform substantially the same function in substantially the same way to achieve substantially the same result that the invention can be practiced with modification within the scope of the following claims.

The invention claimed is:

1. A method for treating a subject having a stomach with a stomach wall surrounding a cavity of the stomach, the method comprising:
    implanting electronic circuitry within the subject;
    supporting a temperature sensor within the cavity of the stomach so as to measure a temperature within the cavity;
    electrically coupling a stimulating electrode to the wall of stomach;
    operatively coupling the circuitry to the temperature sensor;
    operatively coupling the circuitry to the stimulating electrode;
    sensing the temperature within the cavity of the stomach with the temperature sensor;
    determining, using the circuitry and in response to the sensed temperature, a rate of change of the temperature within the cavity of the stomach;
    identifying, using the circuitry and in response to the rate of change of the temperature within the cavity of the stomach, an ingestion of material by the subject; and
    stimulating the stomach by energizing the electrode using the circuitry in response to the identified ingestion of material by the subject.

2. The method of claim 1 further comprising:
    sensing another parameter from the subject; and
    determining, with the circuitry and in response to the other sensed parameter; a condition of the subject, wherein the stimulation of the stomach is performed in response to the determination of the condition of the subject.

3. The method of claim 2, wherein determining the condition of the subject comprises determining whether the subject is sleeping or awake, and wherein stimulation of the stomach is inhibited in response to a determination that the subject is sleeping.

4. The method of claim 2, wherein determining the condition of the subject comprises determining whether the subject is sleeping or awake, and wherein the stimulation of the stomach is performed in response to a determination that the subject is sleeping.

5. The method of claim 2 wherein the other parameter sensed corresponds to muscle contractions of the stomach.

6. The method of claim 5 wherein the other sensor comprises a pressure sensor.

7. The method of claim 2, wherein the temperature sensed from within the cavity of the stomach varies in response to a temperature of the material ingested by the subject.

8. The method of claim 2, wherein supporting the temperature sensor comprises affixing an anchor to the stomach wall with the temperature sensor extending away from the stomach wall and into the interior of the stomach.

9. The method of claim 8, wherein affixing the anchor to the stomach wall is performed using an elongate member extending through the stomach wall by engaging an inner surface of the stomach wall with a first surface coupled to the elongate member, and by engaging an outer surface of the stomach wall with a second surfaces coupled to the elongate member so that the stomach wall is disposed between the first surface and the second surface, and wherein electrically coupling the electrode to the stomach wall is performed by inserting the elongate member through the stomach wall, the electrode being disposed on the elongate member.

* * * * *